United States Patent
Sun et al.

(10) Patent No.: US 11,696,840 B2
(45) Date of Patent: Jul. 11, 2023

(54) KNEE JOINT

(71) Applicant: The University of Tokyo, Tokyo (JP)

(72) Inventors: Xiaojun Sun, Tokyo (JP); Masayuki Inaba, Tokyo (JP); Kei Okada, Tokyo (JP); Yuki Asano, Tokyo (JP)

(73) Assignee: The University of Tokyo, Tokyo (JP)

( * ) Notice: Subject to any disclaimer, the term of this patent is extended or adjusted under 35 U.S.C. 154(b) by 463 days.

(21) Appl. No.: 16/348,435

(22) PCT Filed: Aug. 30, 2017

(86) PCT No.: PCT/JP2017/031190
§ 371 (c)(1),
(2) Date: May 8, 2019

(87) PCT Pub. No.: WO2018/087997
PCT Pub. Date: May 17, 2018

(65) Prior Publication Data
US 2021/0298922 A1 Sep. 30, 2021

(30) Foreign Application Priority Data
Nov. 10, 2016 (JP) ................. 2016-219496

(51) Int. Cl.
*A61F 2/64* (2006.01)
*A61F 2/50* (2006.01)
(Continued)

(52) U.S. Cl.
CPC ........ *A61F 2/64* (2013.01); *A61F 2002/5075* (2013.01); *A61F 2002/6836* (2013.01); *A61F 2002/701* (2013.01)

(58) Field of Classification Search
CPC ........................................ A61F 2/64
See application file for complete search history.

(56) References Cited

U.S. PATENT DOCUMENTS

| 5,650,704 A | 7/1997 | Pratt et al. |
| 5,904,721 A * | 5/1999 | Henry ............... A61F 2/644 623/44 |

(Continued)

FOREIGN PATENT DOCUMENTS

| CN | 101496751 A | 8/2009 |
| EP | 1531766 A1 | 5/2005 |

(Continued)

OTHER PUBLICATIONS

Extended European Search Report for EP 17 86 9954, dated Apr. 7, 2020, 8 pages.

(Continued)

*Primary Examiner* — Jacqueline Woznicki
(74) *Attorney, Agent, or Firm* — Seed Intellectual Property Law Group LLP

(57) ABSTRACT

A knee joint that is capable of widening a moveable range, and that has good energy efficiency and is small and lightweight is described. Also described is a knee joint that is of an active type, but comparatively inexpensive. A drive section moves a driven member. An elastic member is arranged between the driven member and a linear motion member. The linear motion member elastically moves in at least one direction, in accordance with movement of the driven member, by way of the elastic member. A crank mechanism can realize bending and extension of the knee joint by converting linear motion of the linear motion member to rotational motion.

11 Claims, 28 Drawing Sheets

(51) Int. Cl.
  *A61F 2/68*   (2006.01)
  *A61F 2/70*   (2006.01)

(56) References Cited

U.S. PATENT DOCUMENTS

| | | | |
|---|---|---|---|
| 6,673,117 B1* | 1/2004 | Soss | F16F 9/5123 |
| | | | 623/24 |
| 2004/0181289 A1* | 9/2004 | Bedard | A61F 2/64 |
| | | | 623/24 |
| 2007/0050044 A1* | 3/2007 | Haynes | A61F 2/70 |
| | | | 623/24 |
| 2007/0123997 A1 | 5/2007 | Herr et al. | |
| 2010/0312363 A1* | 12/2010 | Herr | A61F 2/70 |
| | | | 623/39 |
| 2011/0098828 A1* | 4/2011 | Balboni | A61F 2/70 |
| | | | 623/40 |
| 2012/0209405 A1 | 8/2012 | Herr et al. | |
| 2015/0374573 A1* | 12/2015 | Horst | A61H 3/00 |
| | | | 602/16 |
| 2016/0158029 A1 | 6/2016 | Kuiken et al. | |

FOREIGN PATENT DOCUMENTS

| | | |
|---|---|---|
| JP | 2004-167106 A | 6/2004 |
| KR | 10-2008-0075465 A | 8/2008 |
| WO | 2004/017871 A2 | 3/2004 |
| WO | 2004/017872 A1 | 3/2004 |

OTHER PUBLICATIONS

Rouse et al., "Clutchable series-elastic actuator: Implications for prosthetic knee design," *The International Journal of Robotics Research* 33(13), 2014, 15 pages.

Flynn et al., "CYBERLEGS Beta-Prosthesis Active Knee System," *IEEE International Conference on Rehabilitation Robotics (ICORR)*, Nanyang Technological University, Singapore, Aug. 11-14, 2015, pp. 410-415.

International Search Report, dated Dec. 5, 2017, for International Application No. PCT/JP2017/031190, 2 pages.

* cited by examiner

KNEE JOINT

BACKGROUND

Technical Field

The present disclosure relates to a knee joint used in a prosthetic leg.

Description of the Related Art

Generally, a prosthetic leg is made up of a socket that is fixed to a section of a leg, a knee joint that is connected to a lower end of the socket, and a grounding part that is connected to a lower end of the knee joint. The knee joint, similar to a human knee joint, is capable of extending and bending within a specified angular range.

As a knee joint drive method, three methods exist, namely a passive method, an electronic control method, and an active method. With a passive method, the wearer moves the prosthetic leg, and the knee joint passively bends/extends using a damper of a hydraulic pressure cylinder or pneumatic cylinder and spring force, etc., in accordance with movement of the prosthetic leg. With an electronic control method, movement resistance to bending and extension of the knee joint is adjusted using electronic control, and operation of the knee joint can be improved. One example of an electronic control method knee joint is shown in Japanese patent laid-open No. 2004-167106. Also, with an active method, by actively controlling bending angle of the knee joint using a motor, knee joint movement for operations such as going up and down stairs is supported.

However, a conventional active method knee joint has a problem in that not only is cost high due to its complicated structure, it is also likely that the wearer will become tired due to the weight. In particular, with a conventional active method knee joint, it is necessary to always operate a motor that is mounted on the knee joint, and since energy efficiency is not good, a large capacity battery is required, which tends to make the knee joint large and heavy.

On the other hand, an active method knee joint that moves a knee joint by converting linear motion from a series elastic actuator to rotational movement using a pulley is disclosed in Elliott J. Rouse, Luke M. Mooney and Hugh M. Herr, "Clutchable series-elastic actuator: Implications for prosthetic knee design," Oct. 9, 2014, doi: 10.1177/0278364914545673, The International Journal of Robotics Research, November 2014 vol. 33 no. 13 1611-1625. With this technology, walking energy is utilized by using a spring of a series elastic actuator, and high energy efficiency is obtained compared to energy efficiency of a conventional active method knee joint. However, with this technology, in order to convert linear motion of the series elastic actuator to rotational motion of the knee, it results in a mechanism that rotates the knee by way of a belt having two pulleys fixed to elastic elements that move linearly. In order to prevent interference between the elastic elements that move linearly and the knee, it is necessary to arrange the belt and pulleys at a side surface of the knee joint. If this is done, then a need arises to use two belts in a single knee joint, in order to maintain balance. Accordingly, with this technology there is a problem that the mechanism becomes extremely complicated, and there are a lot of components. If an angle through which the knee joint can be moved (moveable range) is widened, then the belt and the pulley become large in size, and the knee joint becomes difficult to use due to the size and weight. Also, since a belt for moving the pulleys has a problem from a point of view of durability, there is a tendency for cost to increase easily because of maintenance and replacement of the belt.

Also, a structure for rotatably attaching a knee member to an upper end of a lower limb member, and attaching a foot member to a lower end of the lower limb member, is described in International patent application 2004/017872. A projecting member is integrally formed with a side section of the knee member, and a linear actuator is attached between this projecting member and a lower part of a lower limb member. With this technology it is possible to supplement rotational movement of the knee member using drive force of this linear actuator. However, with this technology, because of the structure where the linear actuator is directly connected to the knee member without a reduction gear, there is problem in that a high load acts on the linear actuator in order to acquire high driving torque.

BRIEF SUMMARY

The present disclosure has been conceived based on the previously described situation. The present disclosure provides a knee joint that is capable of widening a moveable range, and has good energy efficiency and is small and lightweight.

Apparatus for solving the above described problem can be described as in the following aspects.

(Aspect 1)

A knee joint, comprising a drive section, a series elastic mechanism, and a crank mechanism, wherein the series elastic mechanism comprises a driven member, an elastic member, and a linear motion member, the drive section is configured to move the driven member, the elastic member is arranged between the driven member and the linear motion member, the linear motion member is configured to elastically move in at least one direction, in accordance with movement of the driven member, by way of the elastic member, and the crank mechanism is configured to convert linear motion of the linear motion member to rotational motion.

(Aspect 2)

The knee joint of aspect 1, further comprising an upper connection section for connecting a socket and the knee joint, wherein the crank mechanism is configured to cause rotational movement of the upper connection section in forward and backward directions.

(Aspect 3)

The knee joint of aspect 1 and/or aspect 2, further comprising a frame, wherein the linear motion member is capable of movement in at least one direction with respect to the frame.

(Aspect 4)

The knee joint of aspect 1 and/or aspect 2, further comprising a frame, wherein a rotational shaft of the crank mechanism is supported by the frame.

(Aspect 5)

The knee joint of any one of aspect 1 to aspect 4, wherein the drive section comprises a motor, a speed change mechanism, and a ball screw, and wherein the motor is configured to cause rotation of the ball screw in forward and backward directions by way of the speed change mechanism, and the driven member is configured to move linearly in response to rotation of the ball screw.

(Aspect 6)

The knee joint of any one of aspect 1 to aspect 5, wherein the linear motion member comprises a first contact section and a second contact section that are arranged facing each other, either side of the driven member, the elastic member comprises a first spring and a second spring, the first spring is arranged between the first contact section and the driven member, and the second spring is arranged between the second contact section and the driven member.

(Aspect 7)

A prosthetic leg provided with the knee joint of any one of aspect 1 to aspect 6.

According to the present disclosure, it is possible to provide a knee joint that has good energy efficiency, is small and light, and is capable of broadening movement range. Also, according to the present disclosure, it is possible to provide a knee joint that is of an active type, but comparatively inexpensive.

DETAILED DESCRIPTION

A knee joint of one embodiment of the present disclosure will be described in the following with reference to the attached drawings (FIG. 1 to FIG. 10). It should be noted that among these drawings, FIG. 1 to FIG. 5 show a state where a cover 51 (described later) of a frame 5 has been removed, while FIG. 6 to FIG. 10 show a state where the cover 51 has been attached.

Figure 21:
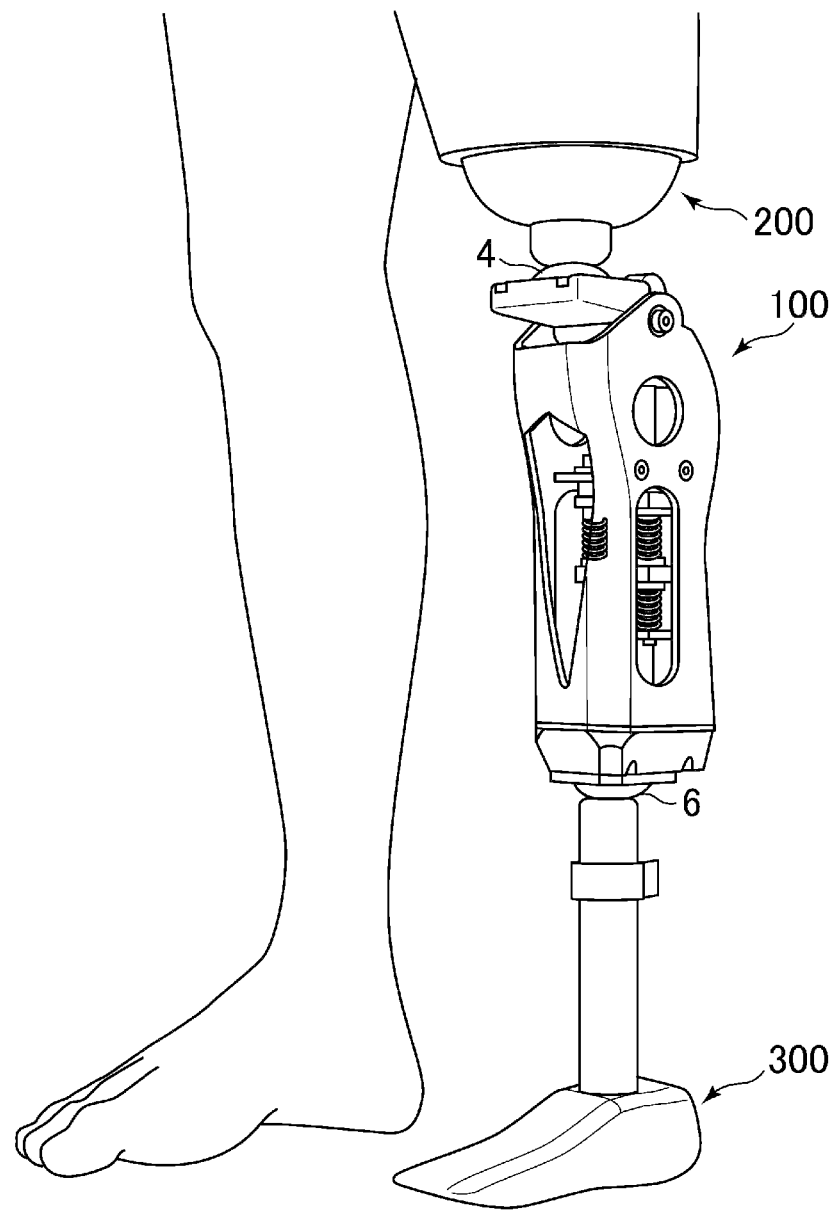
FIG. 21 is a schematic explanatory drawing showing an example of having constructed a prosthetic leg using the knee joint of FIG. 1.

The knee joint 100 of this embodiment can constitute a prosthetic leg by combining a socket 200 and a foot section 300, as shown in FIG. 21 (described later). The structure of the knee joint 100 of this embodiment will be described in the following.

Structure of this Embodiment

The knee joint 100 of this embodiment comprises a drive section 1, a series elastic mechanism 2, and a crank mechanism 3. This knee joint 100 further comprises an upper connection section 4, a frame 5, and a lower connection section 6.

(Drive Section)

The drive section 1 comprises a motor 11, a speed change mechanism 12, and a ball screw 13 (refer to FIG. 5) The motor 11 is configured to cause forward and backward rotation of the ball screw 13 by way of the speed change mechanism 12. The drive section 1 of this embodiment is provided with a battery (not illustrated), and it is possible to drive the motor 11 using electrical power supplied from this battery. However, it is also possible to have a configuration whereby the motor 11 is driven using an external power supply (for example, a commercial power supply). Also, the drive section 1 is provided with sensors (not illustrated) that detect rotation angle of the crank mechanism 3 and load on the motor 11, and it is possible to control torque and rotation angle of the motor 11 in accordance with outputs of these sensors. The motor 11, speed change mechanism 12, and ball screw 13 of this embodiment are supported by the frame 5 via appropriate attachment members or shaft bearings.

(Series Elastic Mechanism)

The series elastic mechanism 2 comprises a driven member 21, an elastic member 22, and a linear motion member 23. The series elastic mechanism 2 of this embodiment also comprises a guide shaft 24 for guiding the driven member 21, and first and second contact sections 231 and 232 of the linear motion member 23.

The driven member 21 is configured to be moved along the guide shaft 24 (in the vertical direction in FIG. 1) by drive force of the drive section 1. More specifically, the driven member 21 of the series elastic mechanism 2 of this embodiment is configured to reciprocate in a linear direction in response to rotation of the ball screw 13 of the drive section 1.

The elastic member 22 is arranged between the driven member 21 and the linear motion member 23. More specifically, the elastic member 22 of this embodiment comprises two first springs 221 and two second springs 222 (refer to FIG. 1 and FIG. 3). The first springs 221 are arranged between the first contact section 231 (described later) of the linear motion member 23 and the driven member 21, but in a state of not being fixed to these members. The second springs 222 are arranged between the second contact section 232 (described later) of the linear motion member 23 and the driven member 21, but in a state of not being fixed to these members.

The linear motion member 23 is configured to elastically move in at least one direction, in accordance with movement of the driven member 21, by way of the elastic member 22. More specifically, as was mentioned previously, the linear motion member 23 of this embodiment is provided with a first contact section 231 and a second contact section 232 that are arranged facing each other either side of the driven member 21, and linear motion rods 233. Also, the first contact section 231 and the second contact section 232 are linked by struts 234 (refer to FIG. 3). Each strut 234 penetrates through a driven member 21, and relative movement is possible between the strut 234 and the driven member 21. Further, each strut 234 is arranged in a state respectively passing through the inside of a first spring 221 and a second spring 222 of the elastic member 22. With this example, bottom ends of the linear motion rods 233 and upper ends of the struts 234 are connected, and these parts constitute an integrated component.

Figure 2:
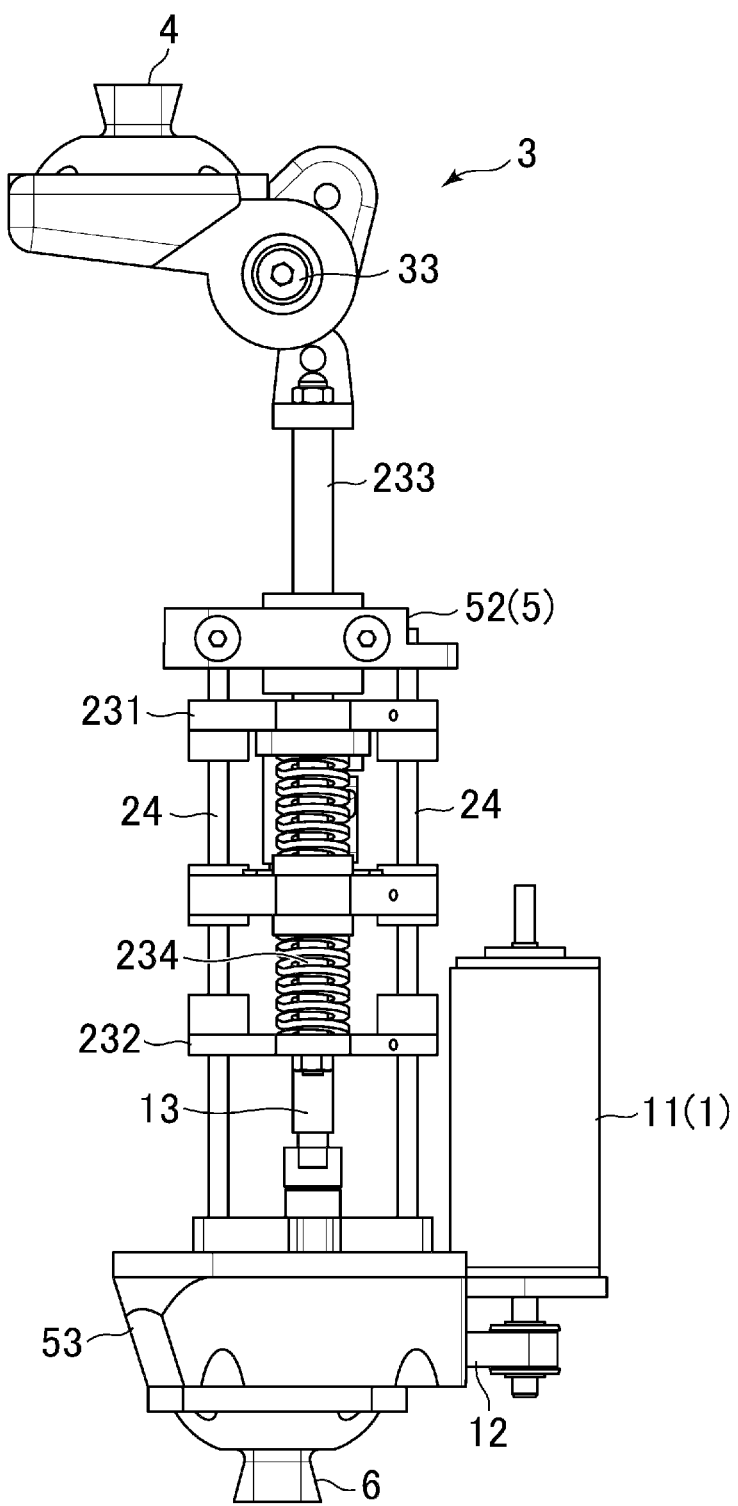
FIG. 2 is a front view of FIG. 1.
Figure 3:
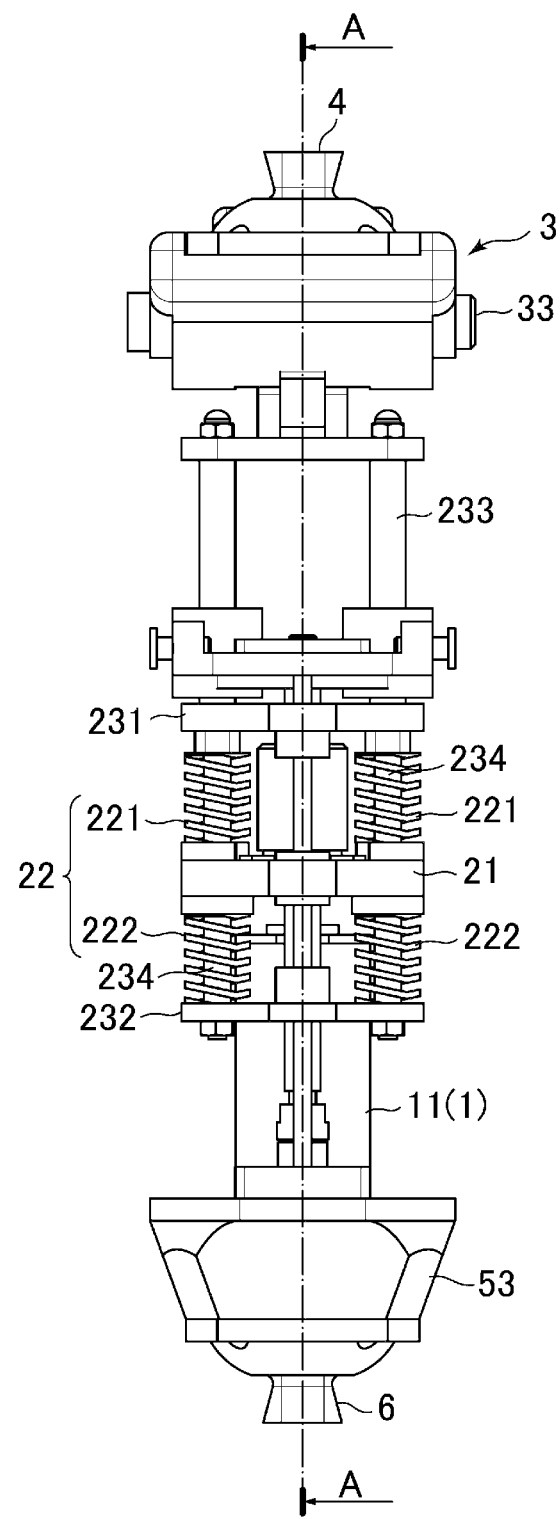
FIG. 3 is a left side view of FIG. 2.
Figure 4:
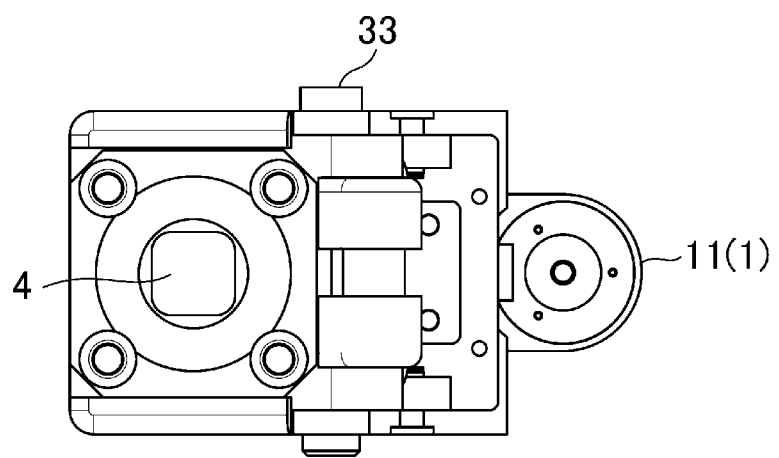
FIG. 4 is a plan view of FIG. 2.
Figure 5:
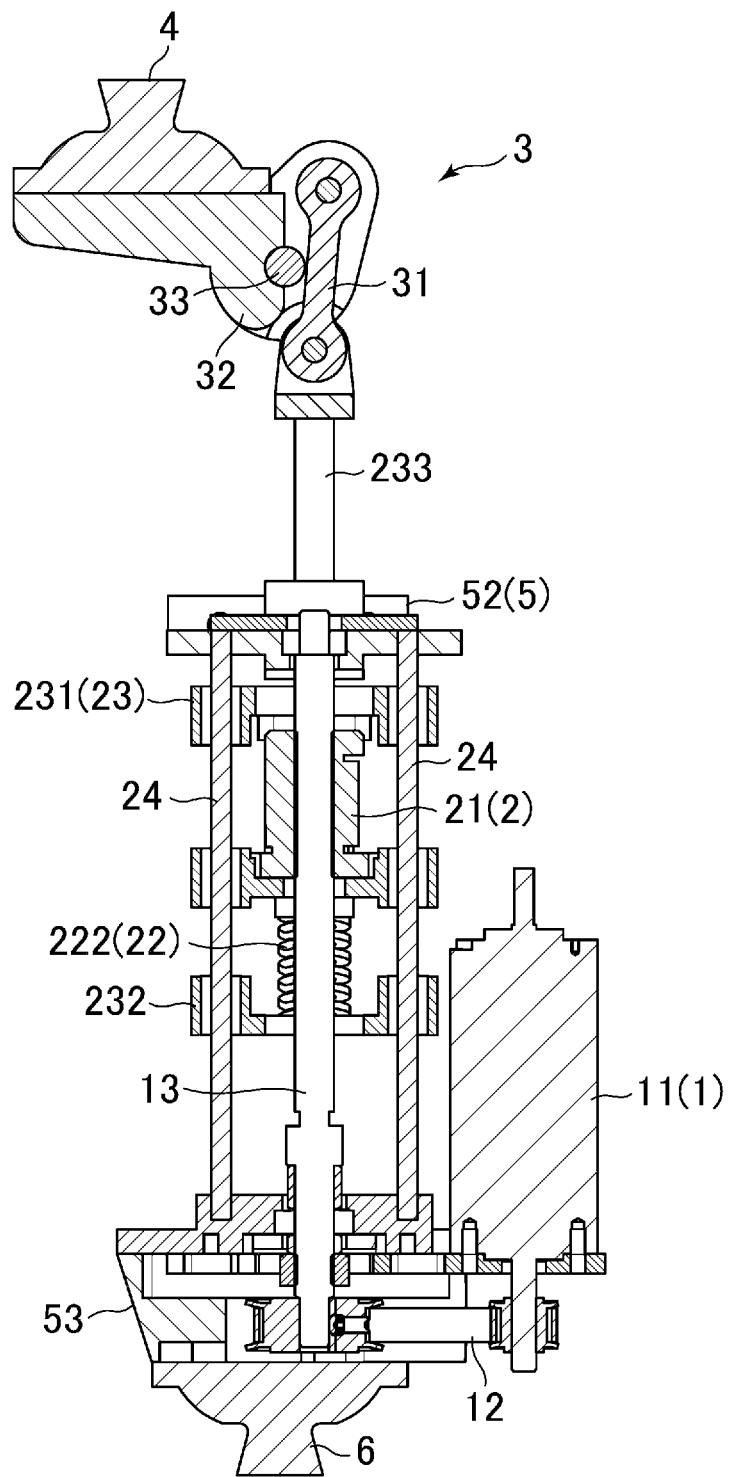
FIG. 5 is a cross sectional view taken along line A-A in FIG. 3.
Figure 6:
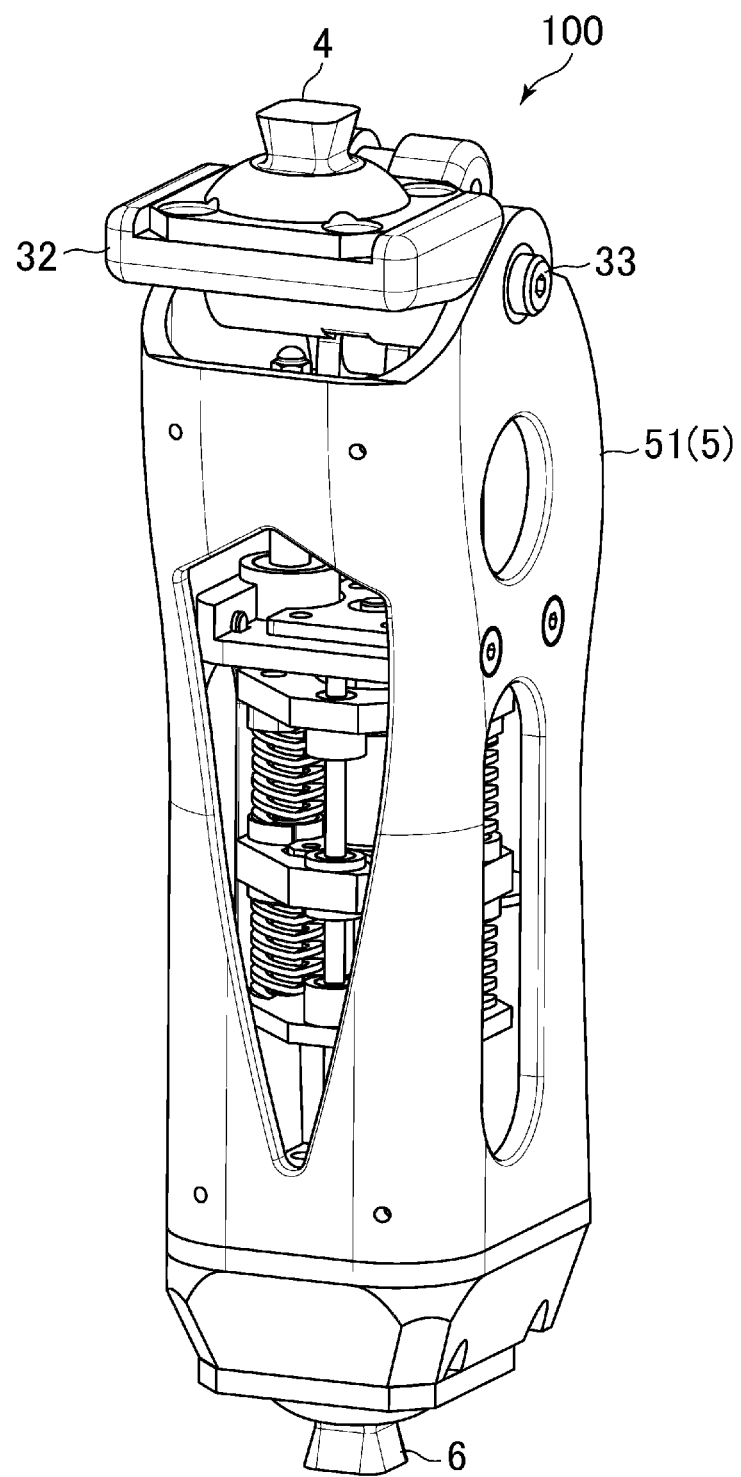
FIG. 6 is a perspective view of the knee joint of FIG. 1 in a state where the cover is attached.
Figure 7:
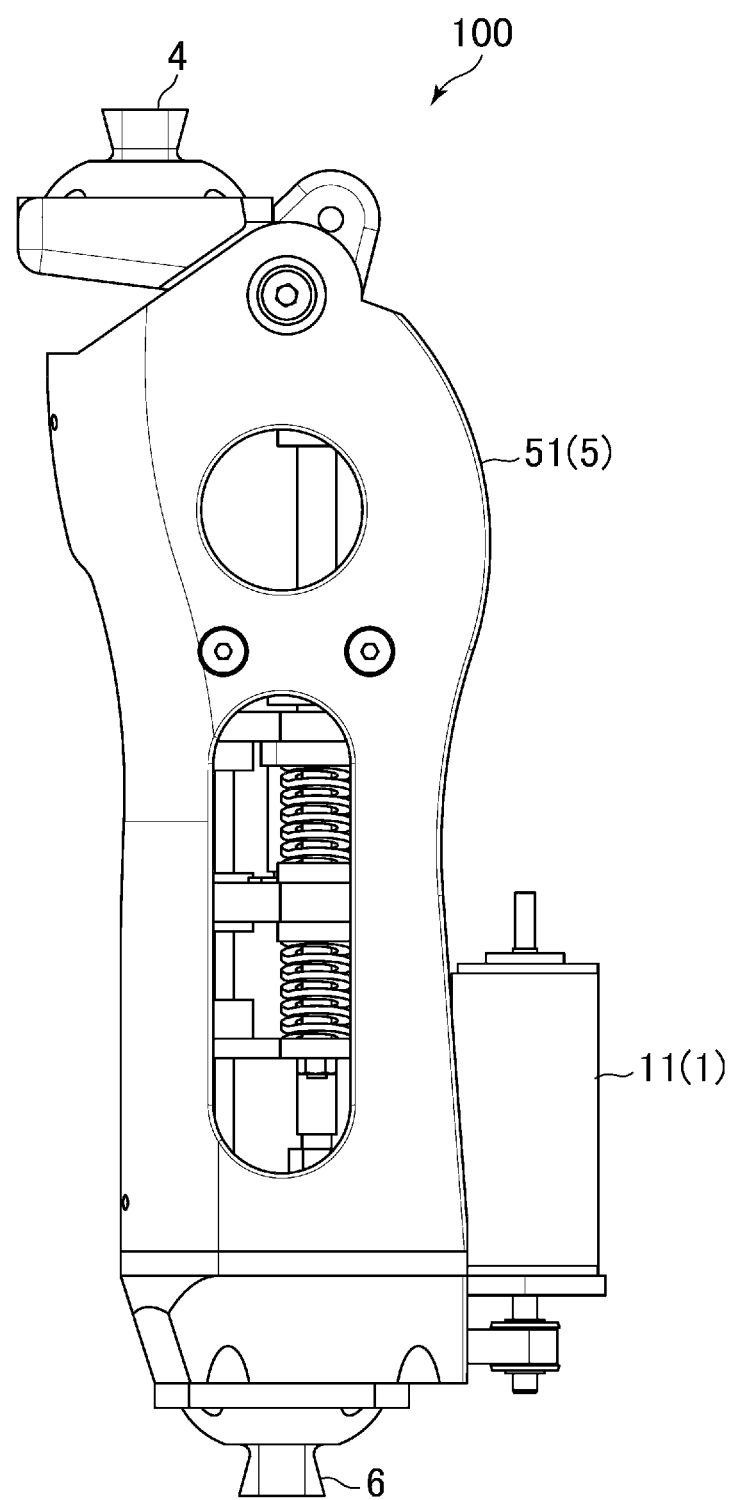
FIG. 7 is a front view of FIG. 6.
Figure 8:
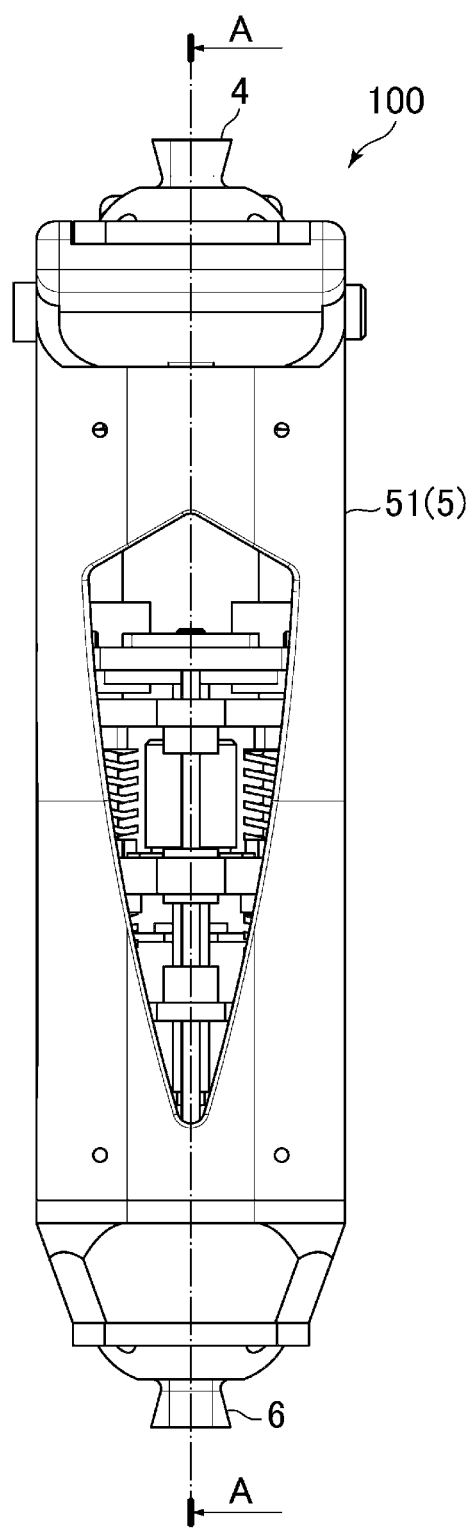
FIG. 8 is a left side view of FIG. 7.
Figure 9:
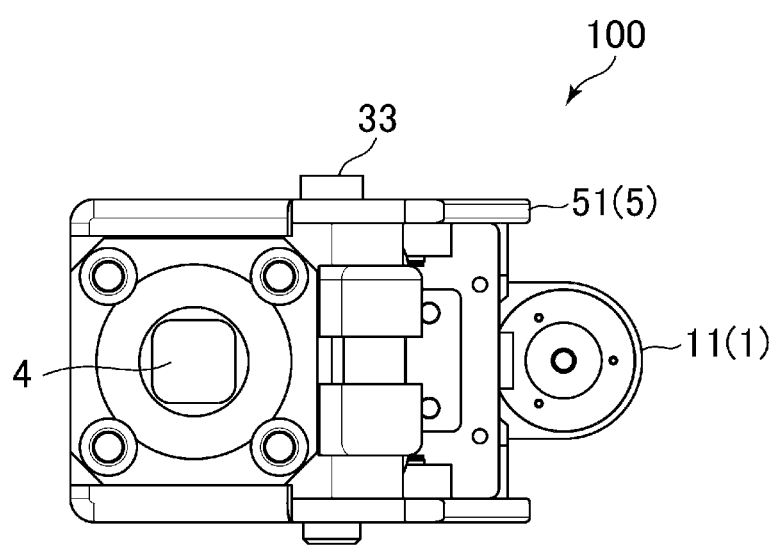
FIG. 9 is a plan view of FIG. 7.
Figure 10:
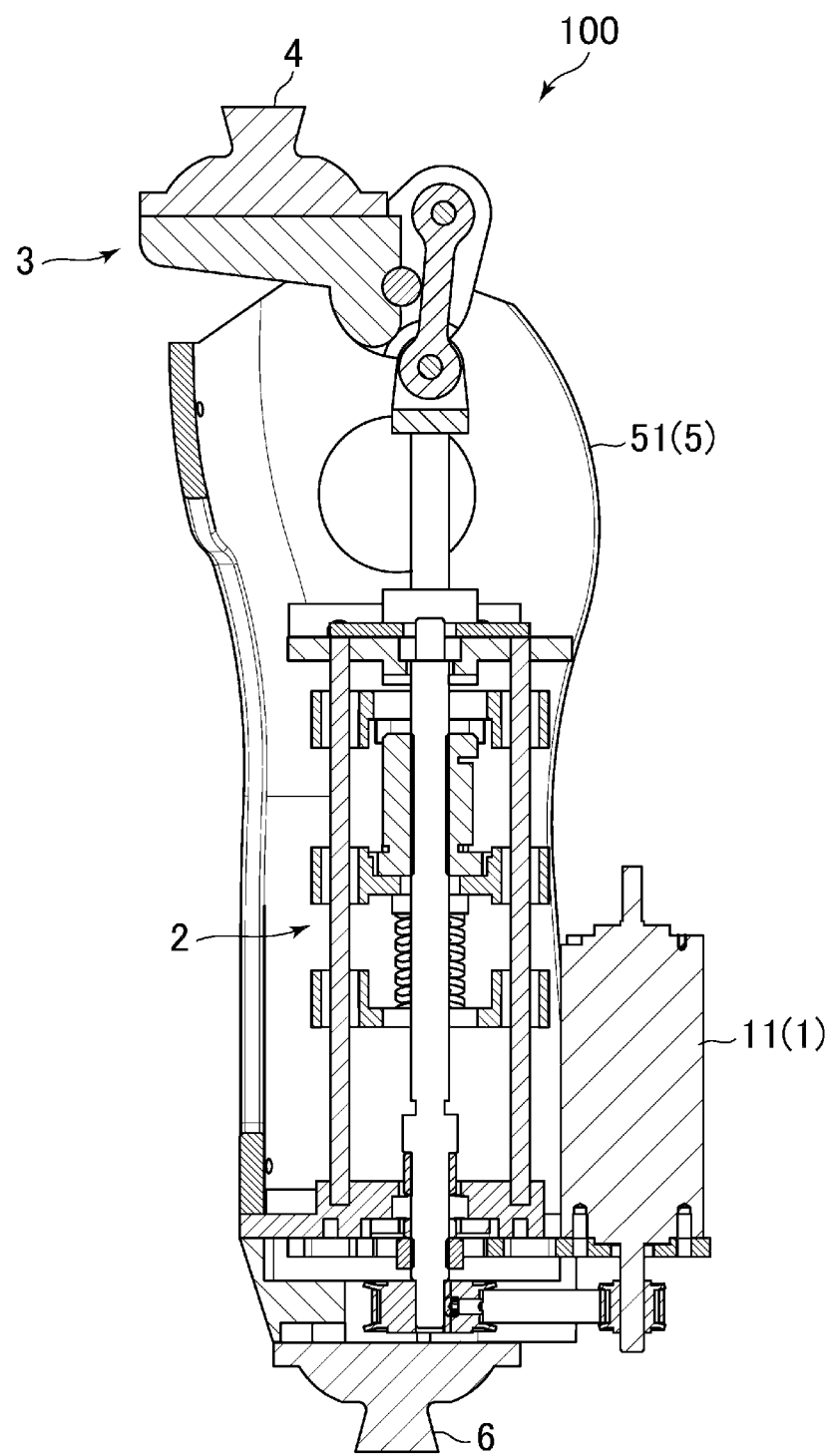
FIG. 10 is a cross sectional view taken along line A-A in FIG. 8.
Figure 11:
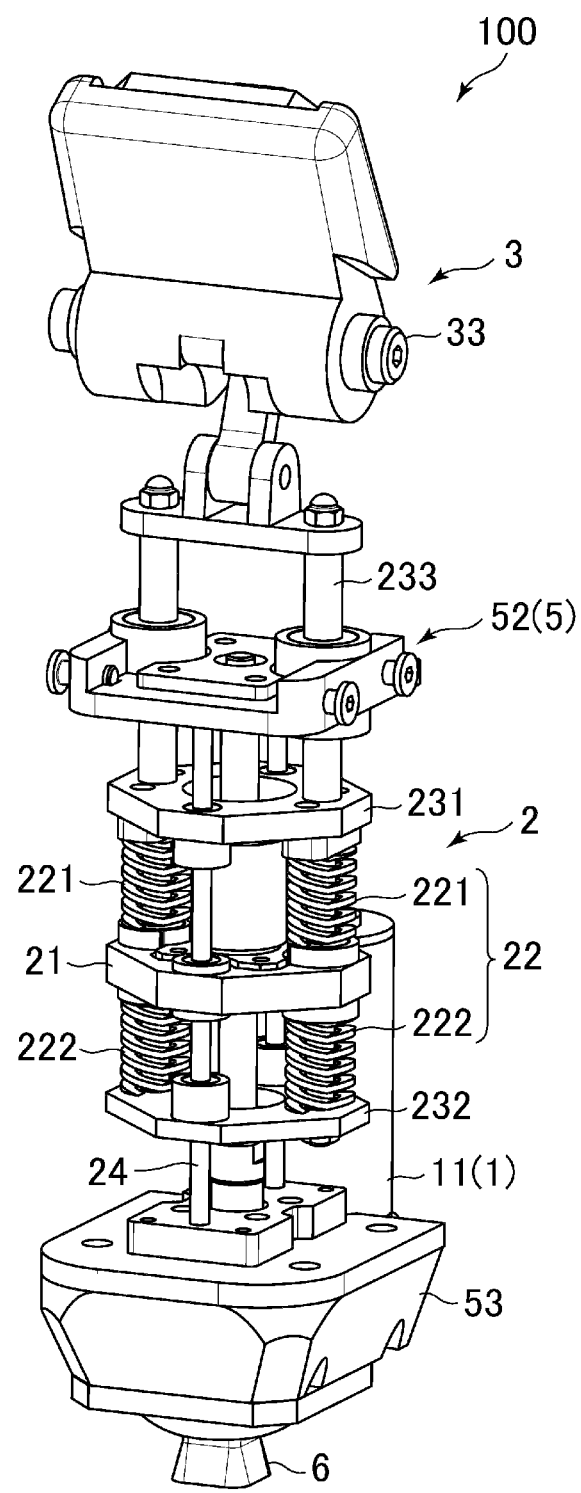
FIG. 11 is a perspective view of the knee joint of FIG. 1, in a state where the bending angle is 60°.

There are two guide shafts 24 in this embodiment, and they are respectively arranged so as to connect an upper base 52 and a lower base 53 (described later) of the frame 5 (refer to FIG. 2). The two guide shafts 24 are not fixed to the driven member 21, the first contact section 231, and the second contact section 232, and in this way it is possible for the driven member 21, the first contact section 231, and the second contact section 232 to move along an extending direction of the guide shafts 24 (that is, in the vertical direction in FIG. 2).

With this embodiment, the linear motion rods 233 of the linear motion member 23 penetrate through the upper base 52 of the frame 5 and are fixed to an upper surface of the first contact section 231 (refer to FIG. 2 and FIG. 3), and reciprocate along the extending direction of the guide shafts 24 (that is, the vertical direction in FIG. 1) in accordance with movement of the first contact section 231 and the second contact section 232.

(Crank Mechanism)

The crank mechanism 3 is configured to convert linear motion of the linear motion member 23 to rotational motion. The crank mechanism 3 of this embodiment comprises a connecting rod 31, an arm member 32, and a rotation shaft 33.

One end of the connecting rod 31 is pin connected to the upper end of the linear motion rods 233 of the linear motion member 23 so as to enable mutual rotation.

The arm member 32 is pin connected to the other end of the connecting rod 31 so as to enable mutual rotation. Also, the arm member 32 is made capable of swinging with the rotation shaft 33 as a center. The upper connection section 4 is attached to an upper part of the arm member 32.

With this embodiment, the rotation shaft 33 is attached to the cover 51 (described later) of the frame 5, and relative position between the rotation shaft 33 and the frame 5 is fixed.

(Upper Connection Section)

The upper connection section 4 is for connecting a socket 200 (refer to FIG. 21 which will be described later) and the knee joint 100. The upper connection section 4 realizes extension and bending operations of the prosthetic leg by rotational movement in forward and backward directions using the crank mechanism 3. The upper connection section 4 is also called a pyramid connector, and it is possible to connect to the socket 200 using an existing method.

(Frame)

The frame 5 of this embodiment comprises the cover 51 (refer to FIG. 6 to FIG. 10), the upper base 52, and the lower base 53. With this embodiment, the linear motion member 23 is made capable of movement in at least one direction with respect to the upper and lower bases 52 and 53 of the frame 5 (specifically, the vertical direction in FIG. 1). Also, with this embodiment, as was mentioned earlier, the rotation shaft 33 of the crank mechanism 3 is supported in a state capable of rotation by the cover 51 of the frame 5. Further, the upper base 52 and the lower base 53 are respectively fixed with respect to the cover 51, so that there is no relative movement.

(Lower Connection Section)

The lower connection section 6 is for connecting a foot section 300 (refer to FIG. 21, which will be described later) and the knee joint 100. The lower connection section 6 is fixed to the lower base 53 of the frame 5. The lower connection section 6 is also called a pyramid connector, and it is possible to connect to the foot section 300 using an existing method.

Operation of this Embodiment

Next, operation of the knee joint 100 of this embodiment will be described with further reference to FIG. 11 to FIG. 22.

(Knee Joint Angle Adjustment Operation . . . 0° to 60°)

Figure 1:
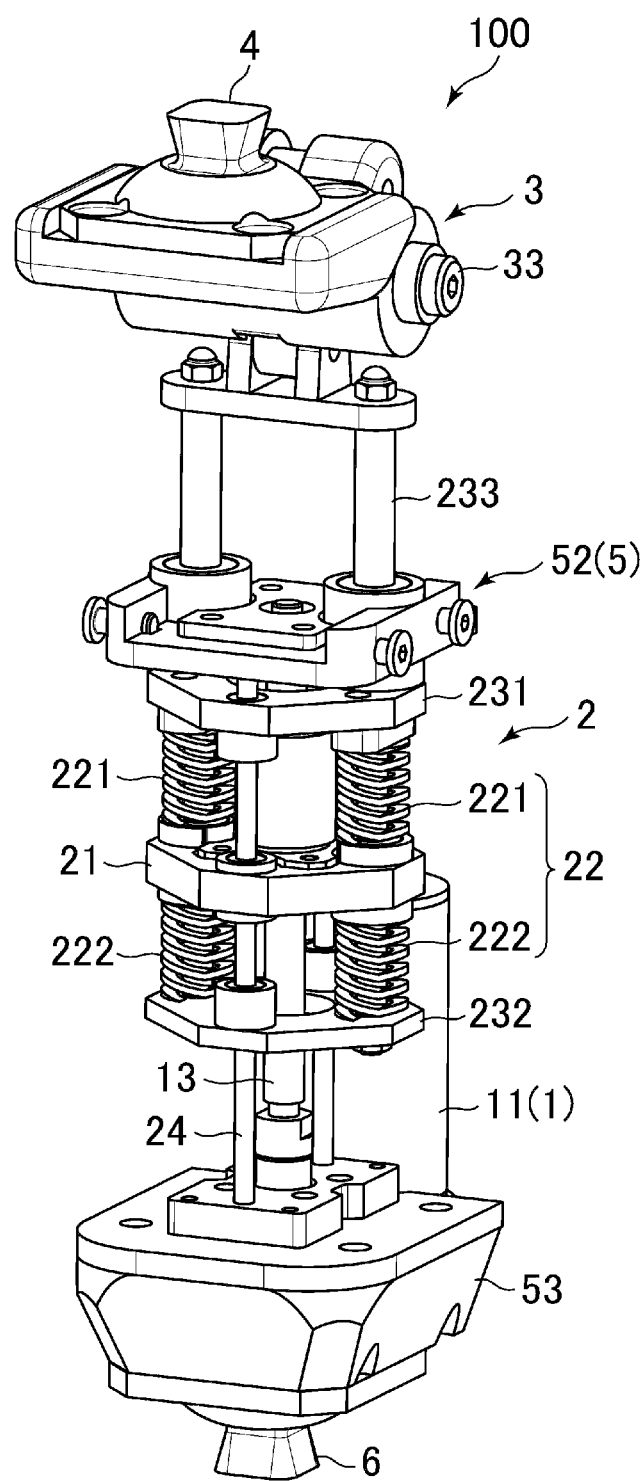
FIG. 1 is a perspective drawing of a knee joint (bending angle=0°) of one embodiment of the present disclosure, in a state with a cover removed.

In the description of this embodiment, the bending state shown in FIG. 1 is defined as the angle of the knee joint being 0°. Operation to bend the bending angle of the knee joint from this state to 60° will be described in the following.

First, the motor 11 of the drive section 1 is made to rotate. If this is done, the ball screw 13 is rotated by way of the speed change mechanism 12, and the driven member 21 of the series elastic mechanism 2 moves in one direction (with this example, the downward direction in FIG. 1).

Once this happens, the driven member 21 applies compression force to the second spring 222 of the elastic member 22, and the linear motion member 23 is moved in one direction (with this example, the downward direction in FIG. 1), by way of this spring. If the linear motion member 23 is lowered by spring force, the connecting rod 31 of the crank mechanism 3 is lowered, and as a result of that lowering the arm member 32 rotates with the rotation shaft 33 as a center (refer to FIG. 11 to FIG. 15). In this way it is possible to cause the upper connection section 4 to rotate by a desired angle. A knee angle of a person walking repeatedly changes from 0° (extended state) to 60° (bent state). Accordingly, after knee bending to 60° the motor 11 is reverse rotated, and the knee returns to the 0° extended state due to the application of compression force to the first spring 221.

(Knee Joint Angle Adjustment Operation . . . 60° to 120°)

Operation from a knee angle of 60° to 120° is operation at the time when the user is seated, sitting in the seiza style (sitting on their legs, or kneeling on the floor). At the time of sitting, in particular, the motor is not operated, but in the case of standing from a seated state, it is possible to provide assistance by operating the motor.

An example of the knee joint having been bent beyond 60° is shown in FIG. 16 to FIG. 20. Similar to the previous description, it is possible to cause bending of the knee joint up to about 120° (ideally up to about 140°) by further rotating the arm member 32 of the crank mechanism 3.

By causing reverse rotation of the motor 11 of the drive section 1, it is possible to return the bending angle of the knee joint to the initial state)(angle=0°.

With this embodiment, it is possible to dynamically change bending angle of the knee joint 100 by appropriately controlling torque, rotation speed, or rotation angle of the motor 11. With usage of the prosthetic leg, for example, when climbing stairs or getting up from a chair, it is possible to support actions of the prosthetic leg user (operations of walking, going up stairs by advancing one step higher on each step with left and right legs alternatively, and standing) by actively controlling rotation angle of the knee joint using drive force of the drive section 1.

Also, with the technology described in the previously mentioned non-patent publication by Elliott J. Rouse, Luke M. Mooney and Hugh M. Herr, "Clutchable series-elastic actuator: Implications for prosthetic knee design," Oct. 9, 2014, doi: 10.1177/0278364914545673, The International Journal of Robotics Research, November 2014 vol. 33 no. 13 1611-1625, there were the following problems.
- a structure for converting linear motion of an elastic mechanism to rotational motion of a knee is extremely complex, and has many components. Accordingly, it becomes heavy;
- if movable angle of the knee joint is widened, a pulley is made large in size;
- in order to prevent interference between component parts (elastic elements) and the knee, it is necessary to arrange a pulley at a side surface of the prosthetic leg. If this is done, then in order to maintain balance a need arises to use two pulley mechanisms in a single prosthetic leg (a single pulley mechanism comprises two pulleys, a single connecting cable, and related components).
- pulley cables have a problem with regard to durability, and it's easy for maintenance costs to become high.

By contrast, according to the knee joint of this embodiment that has been described, it is possible to demonstrate the following advantages:
- since a crank mechanism is used, it is possible to restrict size increase of the knee joint overall even when moveable angle of the knee joint is widened;
- since it is possible to use a single crank mechanism that is small and lightweight instead of the pulley mechanism, it is possible to provide a small and lightweight prosthetic leg;
- a crank mechanism generally has high durability compared to a pulley, and so it is possible to keep maintenance costs low.

(Fitting of the Knee Joint)

Next, an example of the knee joint of this embodiment having been fitted to a user will be described with reference to FIG. 21. With this example, a lower end of the socket 200 is connected to the upper connection section 4 of the knee joint 100, and the foot section 300 is connected to the lower connection section 6 of the knee joint 100. With the illustrated example, the prosthetic leg is made up of the knee joint 100, the socket 200, and the foot section 300. It should be noted that for the connection of the upper connection section 4 and the socket 200, and the connection of the lower connection section 6 and the foot section 300, it is possible to use a similar attachment (not illustrated) to that in the conventional art.

(Walking Operation Using Prosthetic Leg)

Next, a walking operation using the prosthetic leg of this embodiment will be described further referencing FIG. 22. It should be noted that in this drawing reference numeral L has been attached to the prosthetic leg.

Figure 22:
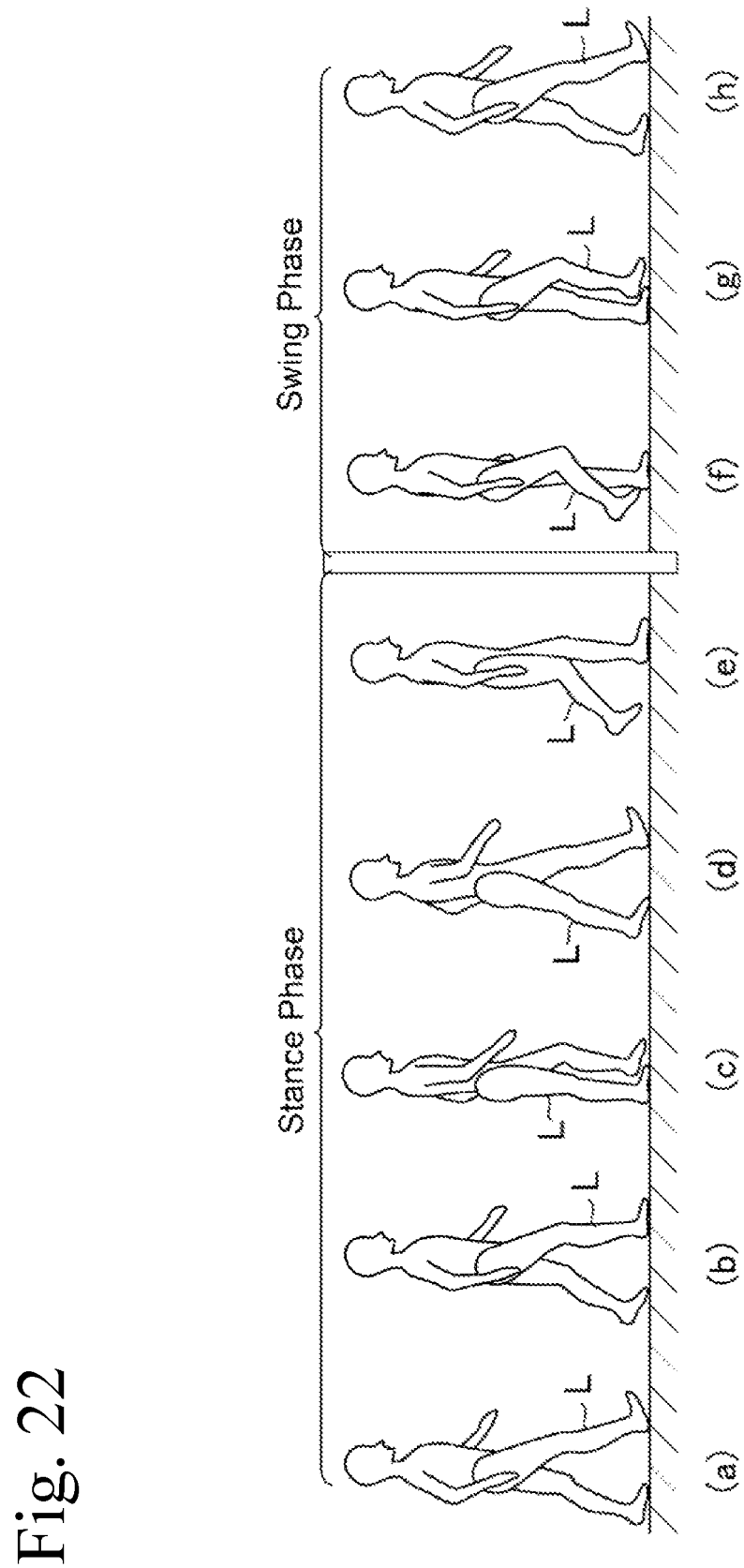
FIG. 22 is an explanatory drawing for describing operation of the prosthetic leg of FIG. 21.

(FIG. 22 (a) to (b))

If the foot section of the prosthetic leg lands on the floor, then with the knee joint of this embodiment, a pressing force is applied downwards on the linear motion member 23 from the socket 200 via the crank mechanism 3, and as a result the first spring 221 of the elastic member 22 is elastically deformed and that energy is stored. However, since the linear motion member 23 is attached to the ball screw 13 via the driven member 21, it is possible to produce a resistance force against movement of the driven member 21 by causing the motor to act in a direction opposite to the direction in which the ball screw rotates, and it is possible to conserve the energy of the elastic member 22.

Here, with this embodiment, by appropriately setting spring force and initial position of the elastic member 22, it is possible to set bending angle (bending angle due to passive deformation) of the knee joint for the time points where the foot section is grounded (FIGS. 22 (a) and (b)) to about 20°. If this is done, there are the advantages in which it is possible to realize a knee bending angle of about 20° for the purpose of impact absorption at the time of grounding that is innate to people, and it is possible to improve usage sensitivity for the user.

Also, with this embodiment, a repulsive force from the floor that has acted on the foot section is transmitted to the user by way of the elastic member 22, which means that it is possible to absorb impact at the time of grounding, and it is possible to reduce advancement of fatigue on the user.

(FIG. 22 (b) to (d))

Continuing on, during a walking operation, the energy that was stored in the elastic member 22 is released. As a result, the linear motion member 23 is caused to move and it is possible to extend the knee joint.

(FIG. 22 (d) to (e))

Figure 12:
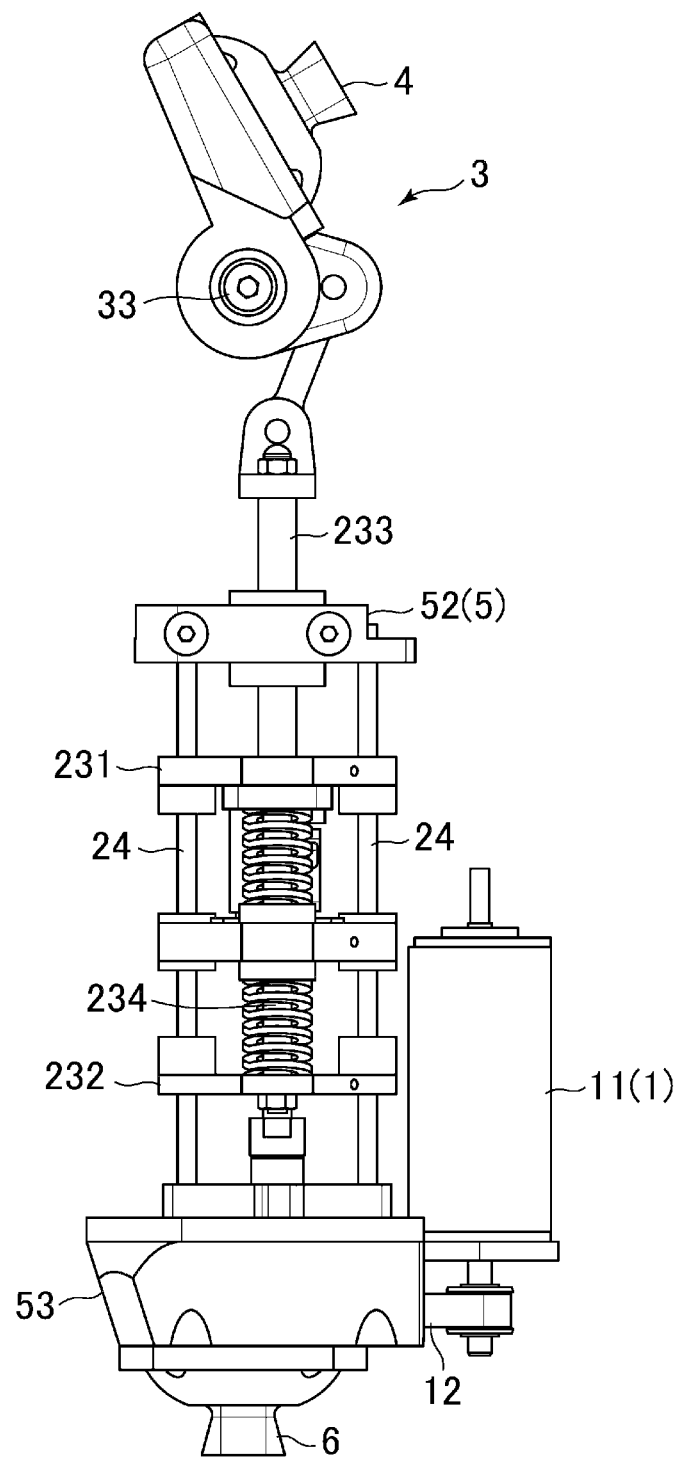
FIG. 12 is a front view of FIG. 11.
Figure 13:
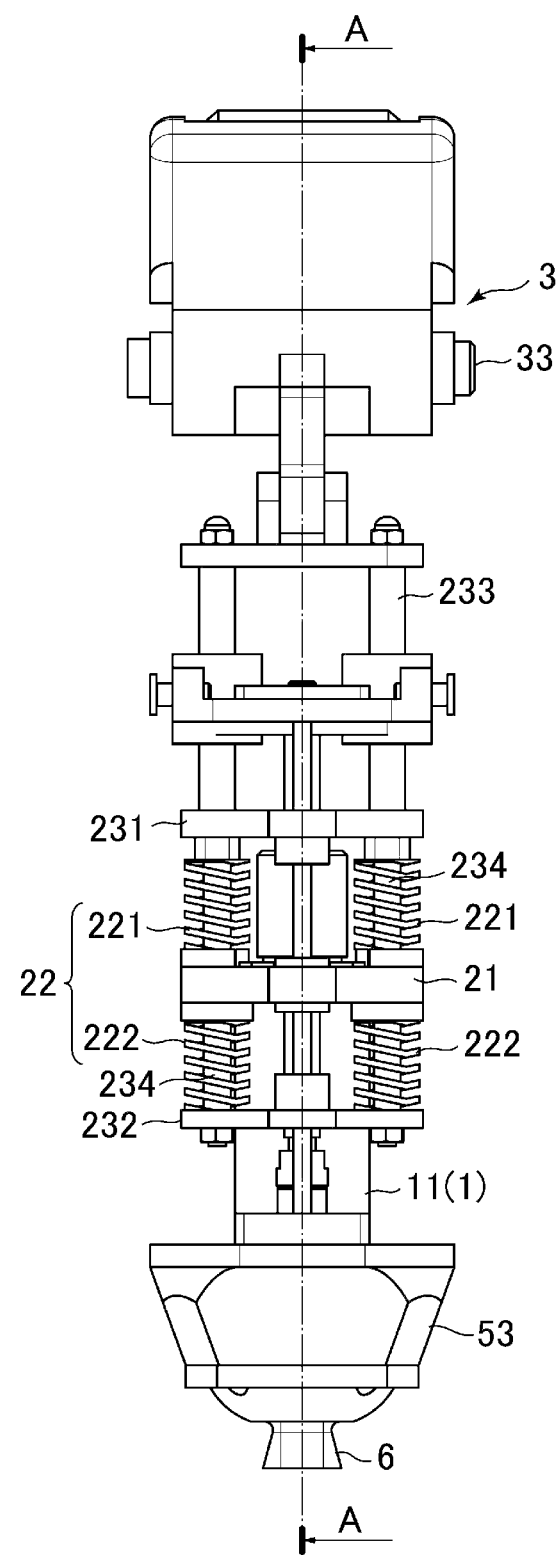
FIG. 13 is a left side view of FIG. 12.
Figure 14:
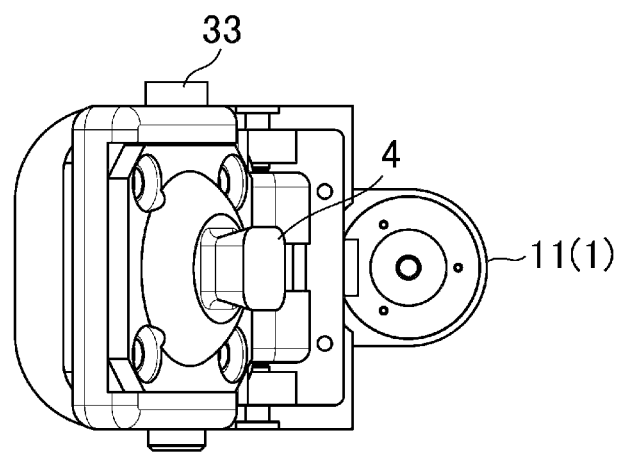
FIG. 14 is a plan view of FIG. 12.
Figure 15:
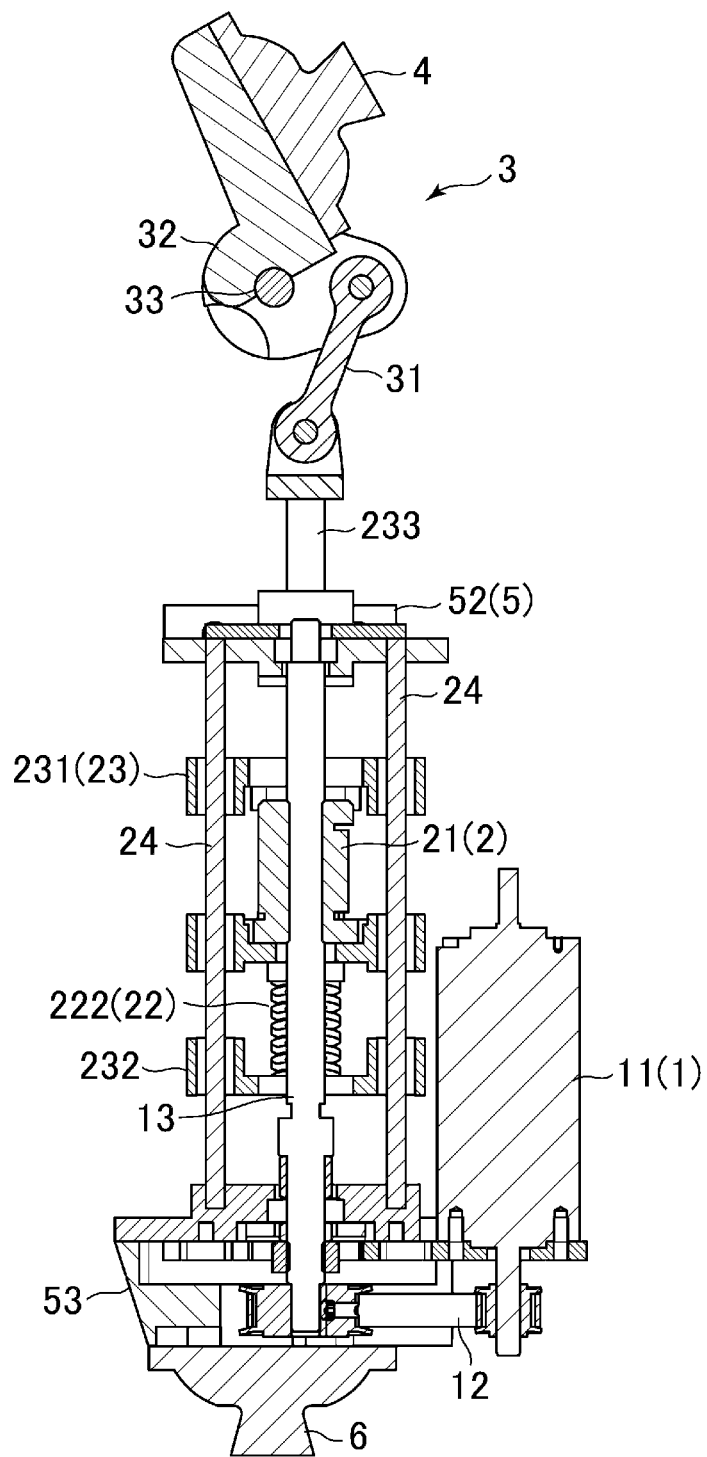
FIG. 15 is a cross sectional view taken along line A-A in FIG. 13.
Figure 16:
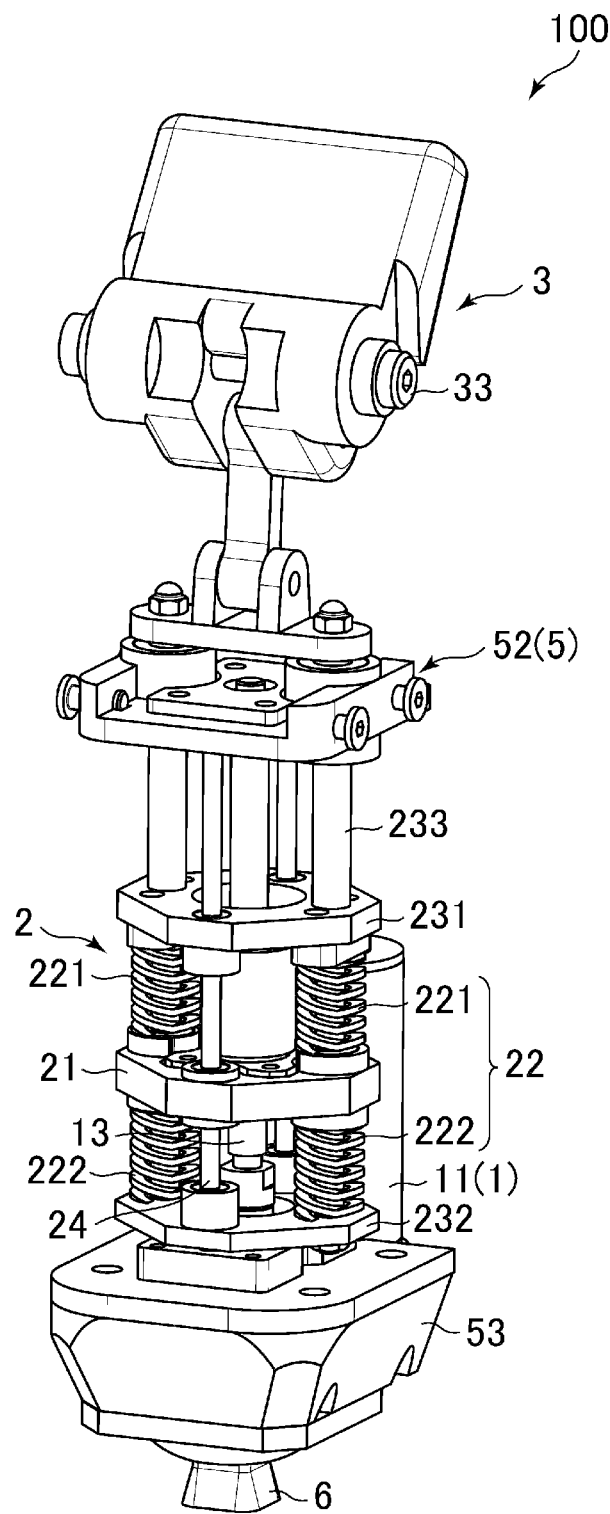
FIG. 16 is a perspective view of the knee joint of FIG. 1, in a state where the bending angle is 120°.
Figure 17:
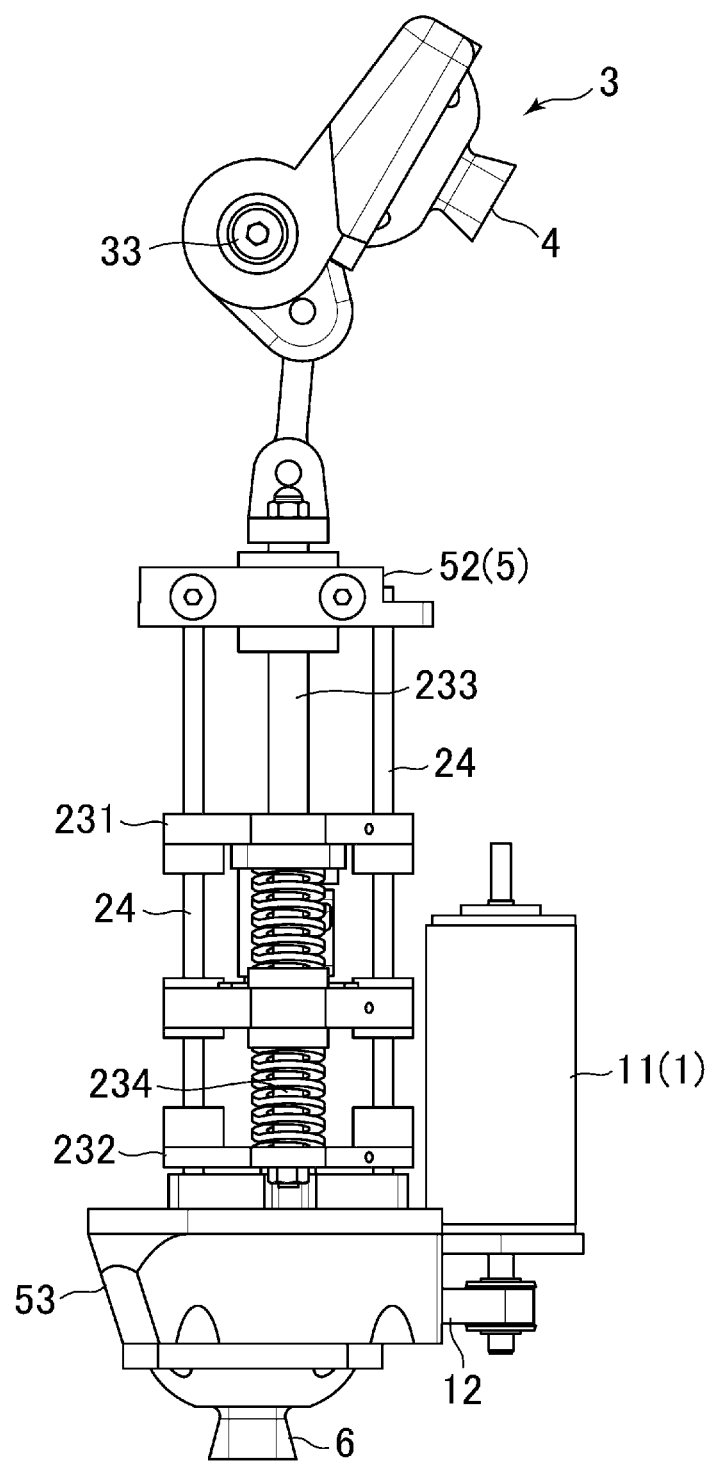
FIG. 17 is a front view of FIG. 16.
Figure 18:
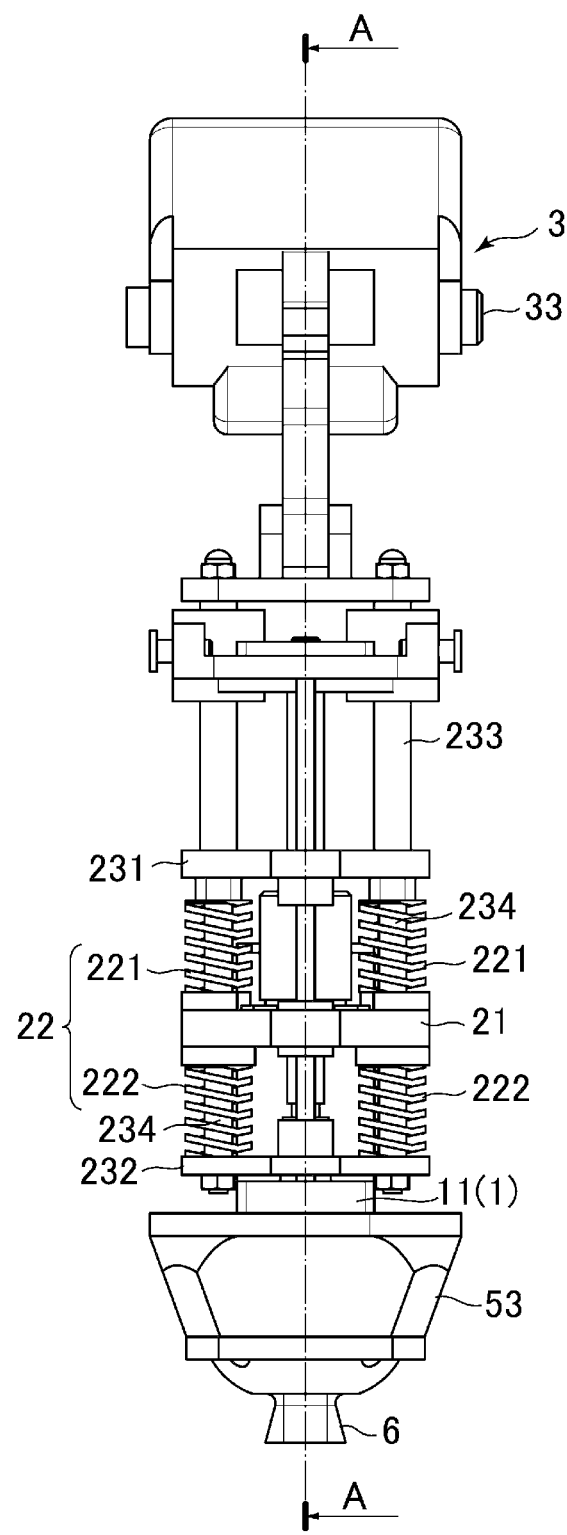
FIG. 18 is a left side view of FIG. 17.
Figure 19:
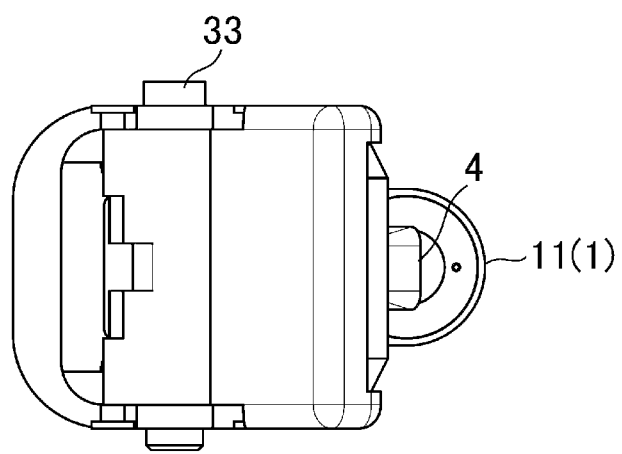
FIG. 19 is a plan view of FIG. 17.
Figure 20:
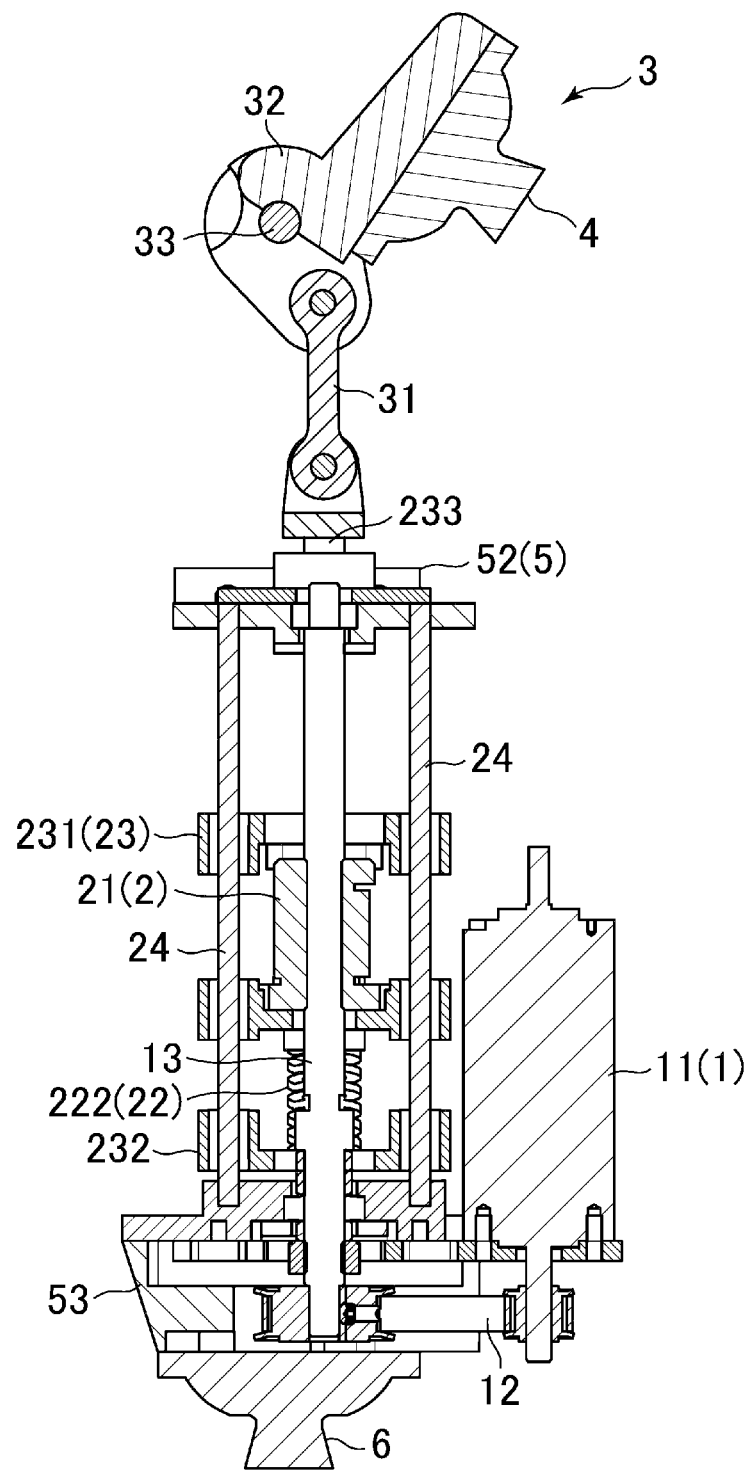
FIG. 20 is a cross sectional view taken along line A-A in FIG. 18.

After that, with this embodiment, the motor 11 is made to operate to bend the knee joint (refer, for example, to FIG. 12). In this way, it is possible to store energy in the elastic member 22.

(FIG. 22 (e) to (f))

If walking advances further, with this embodiment the motor 11 is driven in a reverse direction, and the knee joint is extended. Here, with this embodiment, energy that has been stored in the elastic member 22 supplements the extension operation of the knee joint and so it is possible to reduce the drive force required in the motor 11. Accordingly, with this embodiment battery size reduction and long battery life can be expected.

Also, in a case where friction resistance between the ball screw 13 and the linear motion member 23 has been set low, there is the advantage in which it is possible to perform power regeneration with the motor 11, utilizing elastic force of the previously described elastic member 22.

Next, operation of the crank mechanism 3 of this embodiment will be described in detail with further reference to FIG. 23 to FIG. 28.

Figure 23:
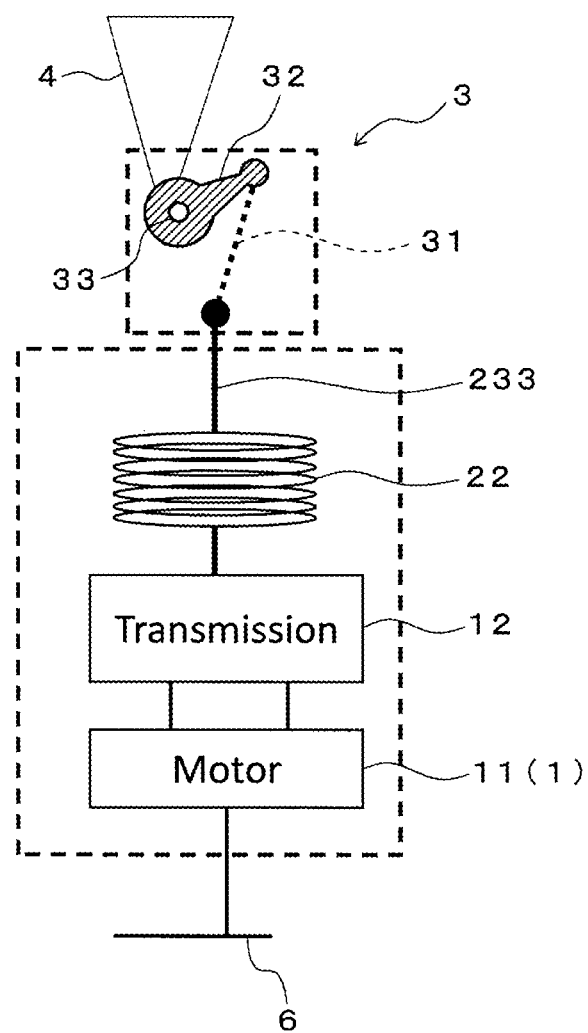
FIG. 23 is an explanatory drawing for describing operation of a crank mechanism of the knee joint of FIG. 1.

First of all, for the purposes of operational description, the structure of the knee joint of the previously described embodiment is schematically shown in FIG. 23. In this diagram, the motor 11, transmission (speed change mechanism) 12, and spring (elastic member) 22 are shown as a single actuator. The mechanism of FIG. 23 is further shown schematically in FIG. 24.

A reduction ratio of the knee joint that uses this crank mechanism 3 is expressed by the following equation.

$$K \frac{2\pi N_b R}{L_b N_m}$$

Here, $N_m$ is the number of teeth of a motor 11 side pulley of the speed change mechanism 12;

$N_b$ is the number of teeth of a ball screw 13 side pulley of the speed change mechanism 12;

$L_b$ is the lead of the ball screw 13;

R is the radius of gyration of the arm member 32; and

K is the reduction coefficient due to crank mechanism.

Here, since each variable other than K is considered to be a constant in this description, detailed description will be omitted. The reduction coefficient K of the crank mechanism is expressed as follows.

$$K = \frac{\text{Sin}(\alpha - \beta)}{\text{Cos}\,\beta}$$

Figure 24:
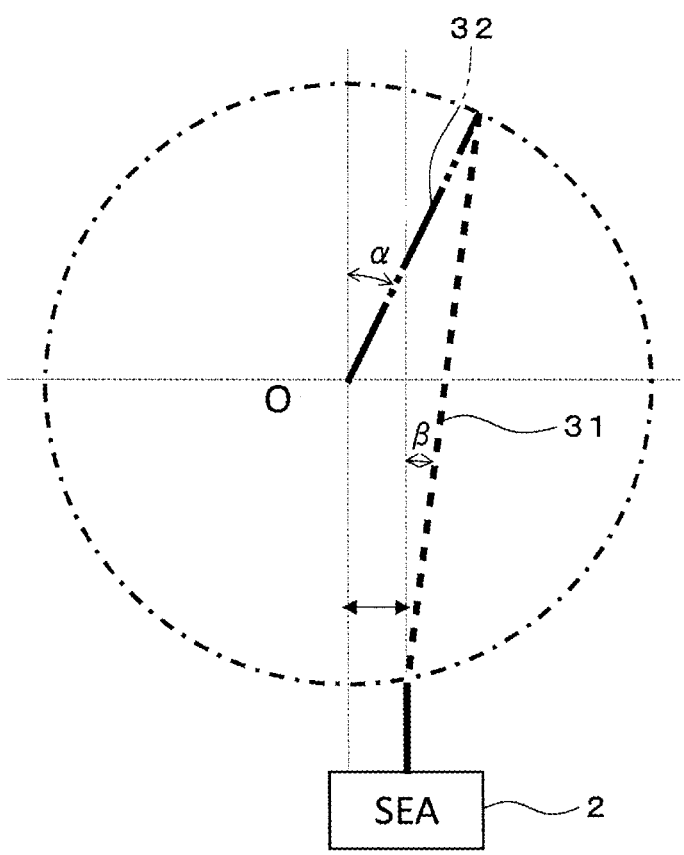
FIG. 24 is a schematic explanatory drawings of the crank mechanism of FIG. 23.

Here,

α is the angle of arm member 32 with respect to the vertical direction (vertical direction in FIG. 24);

β is the angle of connecting rod 31 with respect to vertical direction (vertical direction in FIG. 24).

Figure 25:
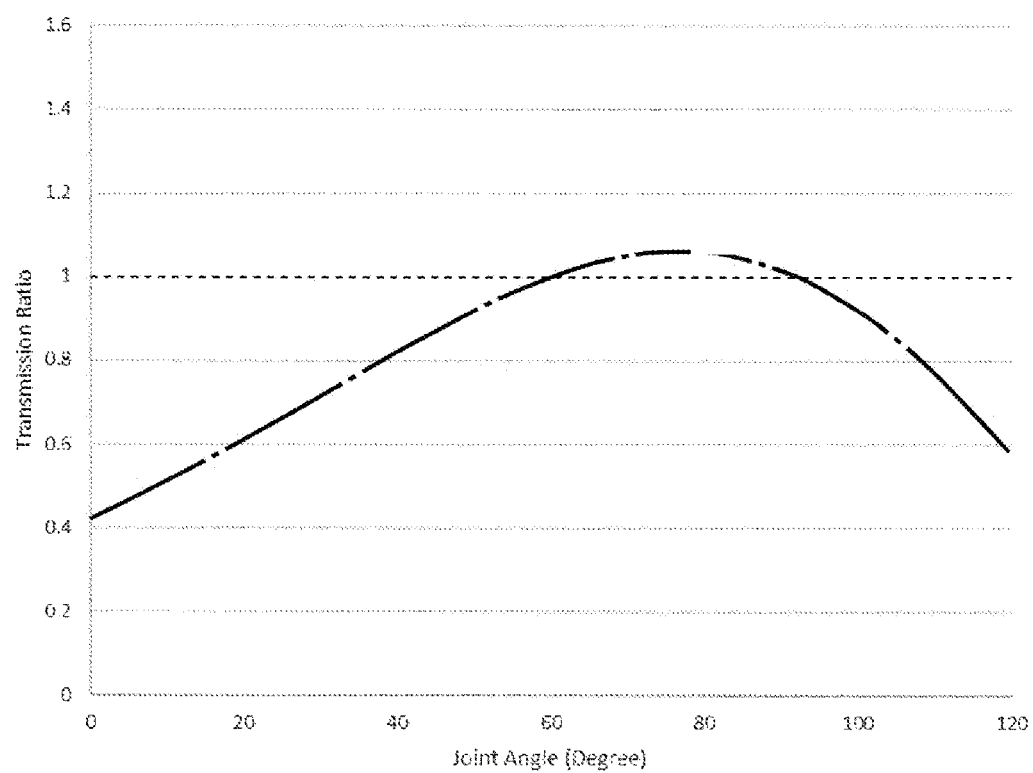
FIG. 25 is a graph showing one example of characteristics of the crank mechanism of FIG. 24, with the horizontal axis showing knee angle (degrees) and the vertical axis showing reduction ratio.

Due to the influence of reduction coefficient K, the reduction ratio of the crank mechanism becomes as shown in FIG. 25. With this characteristic, the reduction ratio changes in accordance with change in knee angle, and the reduction ratio becomes maximum around knee angle α=80° Specifically, with the crank mechanism of this embodiment, it is possible to move the knee joint at a different reduction ratio in accordance with change in the knee angle.

Figure 26:
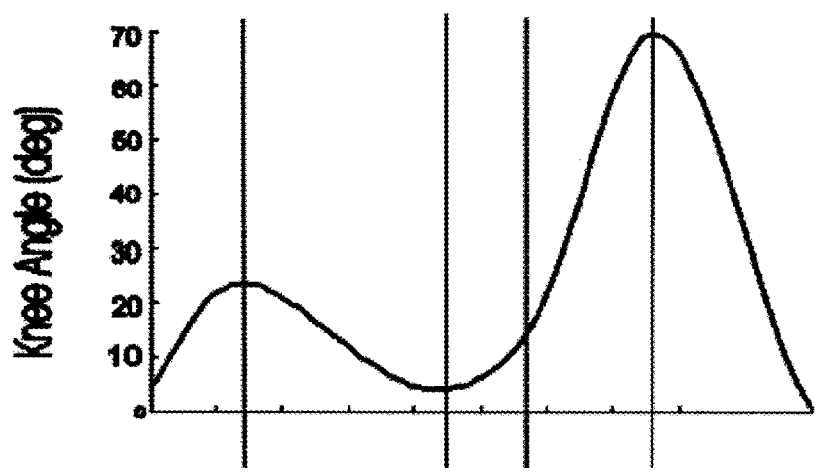
FIG. 26 is a graph showing change in knee angle at the time of walking, with the horizontal axis showing time (arbitrary units) and the vertical axis showing knee angle (degrees).

One example of change over time of knee angle in accordance with a person walking is shown in FIG. 26. As shown in this drawing, during walking, the knee angle changes between about 0° and 80°. Also, for example, when going up and down stairs or standing up from a chair, there is instantaneously a large change from a knee angle of about 80° to a knee angle of about 0°. In a case such as this, where a large angle change is necessary from a deep knee angle, then in order to cause rotation of the knee joint, a large torque becomes necessary. With this embodiment, for a deep knee angle of about 80°, it is possible to obtain a high reduction ratio. If this is done, there is the advantage in which it is possible to provide a large torque to the knee joint without imposing a large load on the motor 11.

Also, in the case of a quick pace, with a knee joint, while a fast rotation speed is required with a shallow knee angle, high torque is not required. With the crank mechanism of this embodiment, in the case of a shallow knee angle (for example, 0° to) 20°, since there is a low reduction ratio there is the advantage in which increasing rotation speed of the knee joint becomes easy.

Conversely, in the case where a pulley mechanism (refer to the previously described non-patent publication by Elliott J. Rouse, Luke M. Mooney and Hugh M. Herr, "Clutchable series-elastic actuator: Implications for prosthetic knee design," Oct. 9, 2014, doi: 10.1177/0278364914545673, The International Journal of Robotics Research, November 2014 vol. 33 no. 13 1611-1625) is used instead of the crank mechanism, then since a reduction coefficient K does not exist in the pulley mechanism, the reduction ratio with the pulley mechanism becomes constant regardless of the knee angle. Accordingly, in the event that large torque is necessary, a large load is liable to arise in the motor. Also, in the case where a speed change mechanism is not used (refer to the previously described International patent application 2004/017872), a similar problem arises. Contrasting with this, with the knee joint of this embodiment, by using the crank mechanism there is the advantage in which it is possible to reconcile high torque and high rotation speed.

Figure 27:
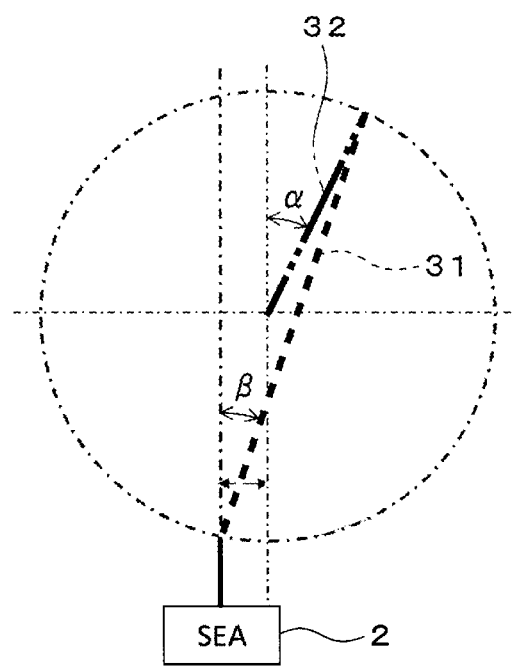
FIG. 27 is an explanatory drawing showing an example where offset amount of a series elastic mechanism with respect to a rotation shaft of a crank mechanism has changed.
Figure 28:
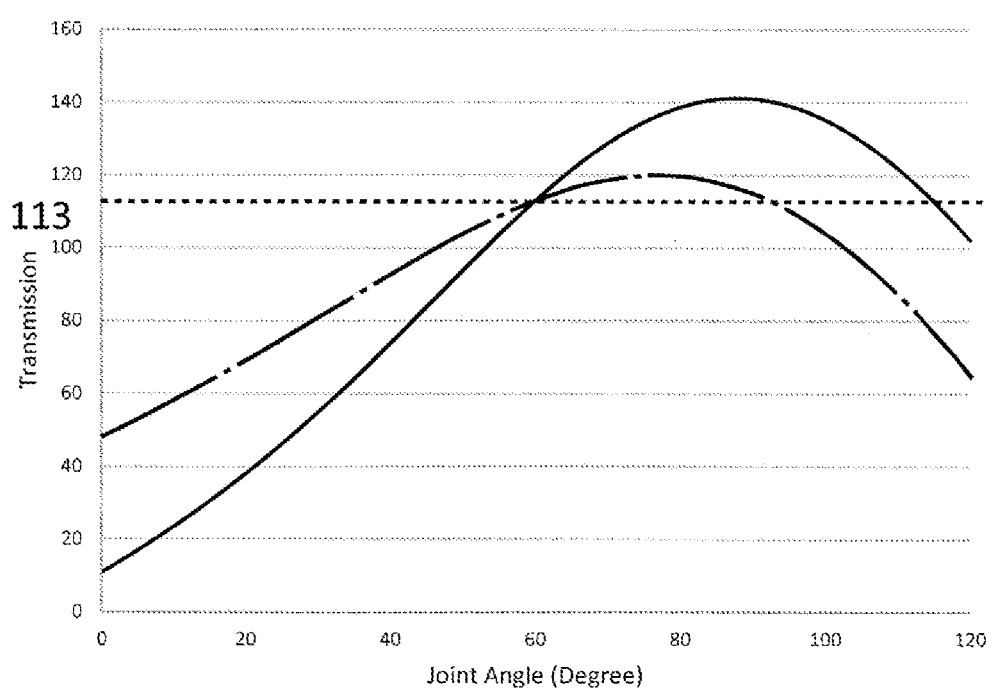
FIG. 28 is a graph showing a characteristic example of the crank mechanism of FIG. 27 overlapped on the characteristic example of FIG. 25, with the horizontal axis showing knee angle (degrees) and the vertical axis showing reduction ratio.

An example where offset amount between center of rotation of the crank mechanism 3 and the series elastic mechanism 2 has been changed is shown in FIG. 27. A characteristic of reduction ratio after change in offset amount is shown by the solid line in FIG. 28. The dot and dash line in FIG. 28 is a characteristic of the example of FIG. 25. As will be understood from this drawing, by changing the offset amount, it is possible to adjust a relationship between knee angle α and reduction ratio. Accordingly, according to this embodiment, there is the advantage in which it becomes possible to obtain maximum torque with the required knee angle, by adjusting the offset amount.

It should be noted that the content of the present disclosure is not limited by the previously described embodiments. The present disclosure may additionally be subject to various changes to the basic structure, within a range disclosed in the scope of the patent claims.

DESCRIPTION OF THE NUMERALS

1 drive section
11 motor
12 speed change mechanism
13 ball screw
2 series elastic mechanism
21 driven member
22 elastic member
221 first spring
222 second spring
23 linear motion member
231 first contact section
232 second contact section
233 linear motion rod
24 guide shaft
3 crank mechanism
31 connecting rod
32 arm member
33 rotation shaft
4 upper connection section
5 frame
51 cover
52 upper base
53 lower base
6 lower connection section
100 knee joint
200 socket
300 foot section
L prosthetic leg The various embodiments described above can be combined to provide further embodiments. All of the patent publications and non-patent publications referred to in this specification and/or listed in the Application Data Sheet are incorporated herein by reference, in their entirety. Aspects of the embodiments can be modified, if necessary to employ concepts of the various publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A knee joint, comprising:
a drive section, a series elastic mechanism, and a crank mechanism, wherein:
the series elastic mechanism comprises a driven member, an elastic member, and a linear motion member;
the driven member is coupled to the drive section and moves in a linear direction when driven by the drive section;
the elastic member is arranged between the driven member and the linear motion member such that the linear motion member is elastically moved by way of the elastic member in the linear direction by movement of the driven member;
the crank mechanism comprises a rotation shaft, a connecting rod, and an arm member, said arm member being rotationally connected to the rotation shaft, and said connecting rod having a first end rotationally connected to the linear motion member and an opposite second end rotationally connected to the arm member, wherein the first end of the connecting rod is displaced by the linear motion member in the linear direction of the movement of the linear motion member and the connecting rod converts linear motion of the linear motion member to rotational motion of the arm member about the rotation shaft; and
the arm member is connected between the second end of the connecting rod and the rotation shaft at an angle α with respect to a vertical axis of the rotation shaft, and the connecting rod is connected to the linear motion member at an angle β with respect to a vertical axis of the linear motion member, wherein the linear motion of the linear motion member is converted to the rotational motion of the arm member according to a reduction ratio that is variable depending on a knee angle of the knee joint, wherein:
the drive section comprises a motor, a transmission, and a ball screw,
the motor is configured to cause rotation of the ball screw in forward and backward directions by way of the transmission, and
the driven member is configured to move linearly in response to rotation of the ball screw, and wherein:
the reduction ratio of the knee joint operates according to the following equation, $$K \frac{2\pi N_b R}{L_b N_m}$$

wherein:
Nm is a number of teeth of a motor side pulley of the transmission;
Nb is a number of teeth of a ball screw side pulley of the transmission;
Lb is a lead of the ball screw;
R is a radius of rotation of the arm member; and
K is a reduction coefficient of the crank mechanism.

2. The knee joint of claim 1, further comprising:
an upper connection section for connecting a socket and the knee joint,
wherein the crank mechanism is configured to cause rotational movement of the upper connection section in forward and backward directions.

3. The knee joint of claim 1, further comprising:
a frame, wherein the linear motion member is capable of movement in the linear direction with respect to the frame.

4. The knee joint of claim 1, further comprising:
a frame, wherein the rotation shaft of the crank mechanism is supported by the frame.

5. The knee joint of claim 1, wherein:
the linear motion member comprises a first contact section and a second contact section that are arranged facing each other on either side of the driven member;
the elastic member comprises a first spring and a second spring;
the first spring is arranged between the first contact section and the driven member; and
the second spring is arranged between the second contact section and the driven member.

6. The knee joint of claim 1, wherein:
the reduction ratio of the crank mechanism is configured to change in accordance with rotation angle for the rotational motion of the arm member.

7. A prosthetic leg provided with the knee joint of claim 1.

8. The knee joint of claim 7, wherein:
movement of the driven member is impeded by resistive force of the drive section when a foot section of the prosthetic leg is landing so that the elastic member accumulates elastic deformation energy for moving the linear motion member to extend the knee joint.

9. The knee joint of claim 8, wherein:
a spring force and an initial position of the elastic member are set to provide the knee angle of the knee joint of around 20 degrees when the foot section is landing.

10. The knee joint of claim 1, wherein:
the linear motion member comprises a first contact section, a second contact section, and linear motion rods, wherein the first contact section and the second contact section are arranged facing each other on either side of the driven member;
the first contact section and the second contact section are linked by struts; and
bottom ends of the linear motion rods and upper ends of the struts are connected as integrated components.

11. The knee joint of claim 1, wherein the reduction coefficient K of the crank mechanism operates according to the following equation, $$K = \frac{\operatorname{Sin}(\alpha - \beta)}{\operatorname{Cos}\beta}.$$

* * * * *